United States Patent [19]

Golwyn

[11] Patent Number: 5,017,575

[45] Date of Patent: May 21, 1991

[54] TREATMENT OF IMMUNOLOGICALLY BASED DISORDERS, SPECIFICALLY CROHN'S DISEASE

[76] Inventor: Daniel H. Golwyn, 701 E. Semoran Blvd., Altamonte Springs, Fla. 32715

[21] Appl. No.: 59,889

[22] Filed: Jun. 9, 1987

[51] Int. Cl.$^5$ ............................................. A61K 34/55
[52] U.S. Cl. ................................................... 514/220
[58] Field of Search ......................................... 514/220

[56] References Cited

U.S. PATENT DOCUMENTS

| | | | |
|---|---|---|---|
| 3,980,789 | 9/1976 | Hester, Jr. | 514/220 |
| 3,980,790 | 9/1976 | Hester, Jr. | 514/220 |
| 4,508,726 | 4/1985 | Coleman | 514/220 |

Primary Examiner—Jerome D. Goldberg
Attorney, Agent, or Firm—Charles A. McClure

[57] ABSTRACT

Means and methods for treating Crohn's disease, as an example of selectively influencing the immune systems of patients afflicted with intractable disorders and thereby abating or relieving the symptoms of such disorders, including many having an autoimmune abnormality or unbalance, such as an excessive concentration of killer T cells or an insufficient concentration of helper T cells or indeed both. A triazolo composition, such as a triazolobenzodiazepine, is administered to such a patient periodically in an amount effective to influence the immune system accordingly and to alleviate such symptoms, whereupon the dosage is gradually reduced to a maintenance level at which the symptoms do not recur but below which such recurrence is likely or certain.

10 Claims, 1 Drawing Sheet

5,017,575

TREATMENT OF IMMUNOLOGICALLY BASED DISORDERS, SPECIFICALLY CROHN'S DISEASE

TECHNICAL FIELD

This invention relates to treatment of Crohn's disease as an example of mammalian—especially human—disorders such as have an apparently immunological basis; it concerns especially alleviating the symptoms of patients having autoimmune system disorders, by treating them with certain drugs.

BACKGROUND

Certain benzodiazepines are known to be depressants of the central nervous system and are accepted in treatment of patients with symptoms ranging from anxiety to panic. Hitherto they have not been recognized as useful in treating immunological unbalance, such as may give rise to a variety of conditions commonly treated with analgesics, emollients, hormones, and steroids, for example.

Many people suffer from such disorders of the skin, mouth, or gastrointestinal tract as psoriasis, recurrent mouth ulcers, and ulcerative colitis for years with little or no relief. Others have even more debilitating afflictions of circulatory, muscular, and nervous systems, for which no successful treatment is known. Moreover, insult may be added to injury as the patients themselves are often characterized by members of the public as "mental" cases deemed responsible for their own symptoms, if only involuntarily.

My invention is directed to relieving at least the symptoms of such disorders and especially of human leucocyte antigen (HLA) related diseases, as by selectively seeking out and eliminating autoimmune abnormality or unbalance responsible for intractability of such disorders when subjected to more conventional treatment. Such disorder exemplified here is Crohn's disease. More general immunological depression or suppression can also be, in at least some instances, susceptible to similar treatment.

SUMMARY OF THE INVENTION

In general, my invention resides in administering to patients having Crohn's disease, as an example of disorders characterized by deleterious abnormal autoimmune reactions a drug effective to reduce the incidence or the severity of their symptoms to tolerable levels, and preferably to eliminate such symptoms. Certain benzodiazepines are examples of such drugs.

More particularly, the invention comprises alleviating the symptoms of Crohn's disease, attributable at least in part to a patient's own immunological abnormality or unbalance—often evident in concentrations of various white blood cells or of immunoglobulins by administering thereto a triazolo compound, preferably one with accepted pharmacological utility, such as a triazolobenzodiazepine.

A summary, relatively non-technical introduction to the human immune system, describing the respective functions of the various white blood cells or lymphocytes, with illustrative graphics, is in the June 1986 NATIONAL GEOGRAPHIC, vol. 169, no. 6, pp. 702–34.

A primary object of the present invention is to relieve the symptoms of various intractable disorders based upon abnormality or unbalance of the human (or other mammalian) autoimmune system.

Another object of this invention is to counteract various manifestations of the Koebner phenomenon, evident in Crohn's disease wherein bits of otherwise normal tissue released into the bloodstream of their host, as by some trauma, are erroneously treated as antigens by the host's autoimmune system, with resultant damage to tissues of such host.

A further object of the invention is to treat effectively with suitable pharmacological compositions such disorders of the gastro-intestinal tract.

Yet another object of the invention is to demonstrate broader applicability of such therapeutic treatment, especially its wide but selective influence upon the autoimmune system in regard to other apparently HLA-related disorders.

A still further object of the invention is to reduce the concentration of so-called "killer T cells" in patients subject to Crohn's disease, as an example of disorders characterized by an abnormally high concentration of such T cells; or to increase the concentration of "helper T cells" in patients subject to disorders characterized by an abnormally low concentration of such T cells; or to increase the concentration ratio of helper T cells to killer T cells—or to suppressor T cells.

Other objects of this invention, together with methods and means for accomplishing the various objects, will be apparent from the following description of preferred embodiments and variants, which are presented here by way of example rather than limitation.

DESCRIPTION OF THE INVENTION

Figure 1:
FIG. 1 is a largely abdominal radiographic view of a human patient with a history of Crohn's disease, taken before treatment according to the present invention.

The present invention undertakes to modify autoimmune activity of humans, other mammals, and perhaps other animals so as to remedy systemic defects or functional errors whose causes or origins are not yet well understood. It is a fundamentally therapeutic method, whose scope is dependent upon factors remaining to be discovered, if and as it grows from its present infancy to broader applicability.

In the present developmental stage of this method, theoretical statements made herein must be incomplete and may be erroneous in a few or more respects. However, as the therapeutic effects of the invention are obtainable in practice, rather than dependent upon any theory, the inventive method should not be prejudiced by whatever academic or theoretical shortcomings this specification may exhibit, whether in mention of apparent immunological linkages of any given disorder or any other explanatory or schematic passage.

Crohn's disease, among at least several dozen disorders of mammals, notably humans, may be characterized as HLA-related (HLA=human leukocyte antigen). See, for example, CECIL'S TEXTBOOK OF MEDICINE, edition of 1985. Many such disorders are deemed to be idiopathic, and although in some cases they may be alleviated by one treatment or another, no generally effective treatment is known for them individually, let alone more generally. Many or most of them exhibit the Koebner phenomenon, as Crohn's disease does further suggesting an immunological linkage. Heretofore, few if any treatments have been generally successful.

Benzodiazepines constitute a well recognized class of cyclic organic chemicals for which methods of preparation and therapeutic utility also are well known. See, for example, such U.S. Pat Nos. as 2,893,992 for chlordiazepoxide; 3,516,988 for clorazepate; 3,102,116, 3,109,843, and 3,136,815 for diazepam; 3,296,249 for lorazepam; 3,109,843 and 3,340,253 for oxazepam, and 3,192,199 and 3,192,200 for prazepam. Under various brand names, these are accepted as tranquilizers or like agents and are 1,4-diazepines with 7-chloro, 5-phenyl substituents and various substituents in some of the lower numbered positions. Perhaps the best known is diazepam under the brand name "Valium" (Hoffman La Roche). Most, if not all, of these compositions are rather mildly addictive.

Another set of 1,4-benzodiazepines differs by having formed along the former 1,2 side (including the nitrogen present there) a five-membered triazolo ring. See U.S. Pat. Nos. 3,701,782 and 3,987,052 for the preparation of such compositions. The members of this set that have both 8-chloro and 1-methyl groups and are, respectively, 6-phenyl and 6-chlorophenyl-substituted are known as alprazolam and triazolam. They are similarly used under the respective brand names of "Xanax" and "Halcion" (both Upjohn). Use of them and of related triazolo compositions, e.g., to induce sleep, is disclosed in U.S. Pat. Nos. 3,980,789 and 3,980,790.

The just mentioned triazolobenzodiazepines are useful in or according to the present invention, as described further below. Moreover, so far as is known, none of the benzodiazepines lacking the triazolo ring is effective against the disorders to which this invention is directed. Indeed, experimental patients successfully treated according to the present invention—and who discontinued such treatment and substituted triazolo-free benzodiazepines as the tranquilizers of their choice—suffered recurrence of the symptoms they had just been rid of, whereupon resumption of treatment with a triazolobenzodiazepine at a low or maintenance-level dosage again rid them of such symptoms and kept them symptom-free.

Figure 2:
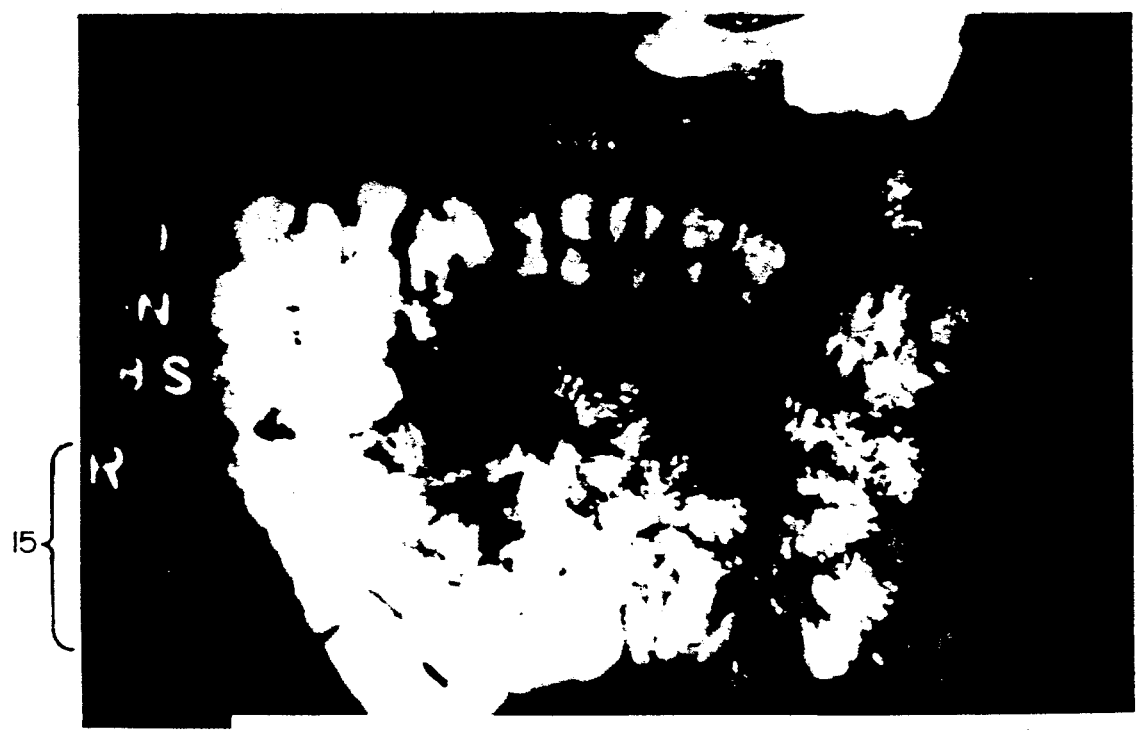
FIG. 2 is a similar view of the same patient, taken after treatment according to this invention.

FIGS. 1 and 2 are abdominal radiographic views of a person with a history (at least ten years) of recurrent psoriasis and chronic ileitis and were taken, respectively, before and after treatment according to the present invention. Visible in both views are a plurality of staples 11, which were introduced upon previous resection of the small intestine. As is common in such disorder, removal of an affected portion of the intestine was followed by a like disorder of at least part of the remainder, a common manifestation of the Koebner phenomenon.

FIG. 1 shows some twenty centimeters of diseased terminal ileum 15 at the left center. The affected portion is narrowed, with an irregular outline characteristic of extreme ulceration.

First, this patient was weaned from all other medication. Then she was given alprazolam daily in increasing dosage, which peaked at 7 milligrams. Within several weeks, after substantial reduction in symptoms, such dosage was reduced by a half milligram every several days to less than a single mg daily to maintain her symptom-free. Drowsiness was the only significant side effect.

FIG. 2 was taken four months later, when her psoriasis and intestinal distress had disappeared. This view shows a normally wide and smooth appearance of the formerly diseased part, and the fact of complete healing was confirmed by internal examination.

Effective compositions for use according to this invention are broadly triazolobenzodiazepines, whose preparation is disclosed in aforementioned U.S. Pat. Nos. 3,701,782 and 3,987,052, preferably those further considered in U.S. Pat. Nos. 3,980,789 and 3,980,790. Thus, the compositions of preference for such use herein comprise 8-chloro-1-methyl-6-phenyl-4H-s-triazolo[1,4]-benzodiazepine and 8-chloro-1-methyl-6-(o-chlorophenyl)-4H-s-triazolo[1,4]-benzodiazepine, including their N-oxides and pharmacologically acceptable acid addition salts in combination with a pharmaceutical carrier.

The customary dosage according to this invention is from about five or six to ten or twelve milligrams per day, orally in single or divided doses, or up to several times the approved dose for treating anxiety, etc. An initial dosage of several mg can be readily stepped up to such customary dosage—as compared with the otherwise accepted dosage and, after an effective period of time, be stepped down to maintenance dosage. Gradual reduction, such as by a half milligram every several days, is desirable to minimize withdrawal symptoms in event of addiction.

The need for continuing minimal dosage to prevent recurrence of Crohn's disease symptoms indicates that whatever causes these disorders is in some way interfered with by treatment according to this invention, but the potential for producing such symptoms is not eliminated. In other words, this treatment is an alleviant, not a cure. What appears to be involved is suggested by lymphocyte profiles obtained for patients so afflicted, which customarily show killer T cells, to constitute an abnormally high percentage—of all lymphocytes—viz., more than a generally acceptable maximum in the mid-teens, or which show an abnormally low concentration (less than about 30%) of helper T cells.

Treatment according to this invention has been observed to lower the killer T-cell concentration in such patients, as by as much as one-half of an abnormally high percentage, restoring it to the normal range. Such treatment has also been observed to increase the helper T-cell concentration to as much as three times an initially unacceptably low level.

Whether the killer T-cell concentration decreases, or the helper T-cell concentration increases, or both, the ratio of helper-to-killer T cells increases, as does the ratio of helper to suppressor T cells. In patients with disorders as discussed herein, an initial helper-to-suppressor ratio as low as from about one-half to less than one is often encountered, whereas generally desirable values of such ratio are from about 1.33 to 2.75 or so. Treatment according to this invention raises the ratio, usually sufficiently to restore it to the normal range.

Until a more effective method is discovered, such as actually preventing occurrence of such an immunological unbalance—which so often gives rise to injury or destruction of the host's own normal tissues—this treatment will enable such self-damage potential to be offset, perhaps indefinitely into the future. The consequences for the afflicted patient are obviously very beneficial.

Alternative embodiments of the compositions useful according to the present invention are noted above.

Guidelines for the identification of additional such compositions are presented.

Effectively treated with such suitable pharmacological compositions have been such disorders of the skin, mouth, and gastro-intestinal tract as alopecia, psoriasis, recurrent aphthous stomatitis (mouth ulcers), and ulcerative colitis, as well as Crohn's disease; and likewise such debilitating disorders such as multiple sclerosis, myasthenia gravis, discoid and systemic lupus erythematosis, and polymalgia rheumatica. Reduction in killer T-cell concentration appears to leave only enough such cells to perform their normal functions, as upon high-priority exogenous matter, with the host's own tissues formerly attacked being ignored unless and until the killer T-cell concentration should rise again, as upon discontinuation of the treatment.

Other types of immunological abnormality or unbalance for the application of this invention include (a) allergies, wherein immunoglobulins react to pollens and other relatively innocuous allergens but annoy the host by releasing histamines, etc.; and (b) depressed or suppressed immune systems, such as have been subjected to chemotherapy for treatment of various types of cancer, for example; and (c) those undergoing viral attack of such nature or intensity as to interfere with or overwhelm the functioning of the immune system, such as in certain herpes and influenza strains, also in autoimmune deficiency syndrome (AIDS) which especially depresses helper T cells. Experimental work with AIDS patients according to this invention is under way.

Advantages of this invention are obvious, in view of the extremely injurious or deadly nature of the symptoms amenable to treatment by the compositions and the methods of this invention. Specific therapeutic benefits have been mentioned hereinabove.

Modifications may be made, as by adding, combining, or subtracting compositions or substituents of compositions, or by otherwise varying the treatment method disclosed herein, while retaining at least some of the benefits of the present invention, which itself is defined in the following claims.

I claim:

1. A method of treating a patient for Crohn's disease, wherein the lymphocyte profile of such patient is characterized by an abnormally low initial concentration of helper T cells, comprising administering to such patient a triazolo composition from the class consisting of alprazolam and triazolam in an amount effective to restore such T-cell concentration toward a normal level.

2. Therapeutic method according to claim 1, wherein such T-cell concentration is increased to several times such initially low value.

3. Therapeutic method according to claim 1, wherein a low dosage level is maintained after relief of such symptoms to prevent recurrence thereof.

4. The method of claim 1, wherein such administration results in a helper T-cell concentration approximately triple the abnormally low initial concentration thereof.

5. The method of claim 4, wherein such resulting helper T-cell concentration is at least about thirty percent.

6. Method of treating patients with disorders having as a symptom the Koebner phenomenon, comprising administering to such a patient, wherein such disorder is Crohn's disease, an amount of a composition effective to alleviate such symptom, wherein such composition includes alprazolam.

7. Method of treating patients with disorders having as a symptom the Koebner phenomenon, comprising administering to such a patient, wherein such disorder is Crohn's disease, an amount of a composition effective to alleviate such symptom, wherein such composition includes triazolam.

8. Method of treating patients for Crohn's disease, comprising administering one or more triazolodiazepine compositions, in combination with a pharmaceutical carrier, to humans having as a symptom thereof an abnormally high concentration of killer T-cells in their lymphocyte profile, in amount effective to reduce such T-cell concentration and to relieve such symptom, selected from the class consisting of 8-chloro-1-methyl-6-phenyl-4H-s-triazolo[1,4]-benzodiazepine and 8-chloro-1-methyl-6-(o-chlorophenyl)-4H-s-triazolo[1,4]-benzodiazepine, their N-oxides and pharmaceutically acceptable salts.

9. Therapeutic method according to claim 8, wherein such T-cell concentration is reduced by about half of such initially high value to a normal level.

10. Therapeutic method according to claim 8, wherein a low dosage level is maintained after relief of such symptoms to prevent recurrence thereof.

* * * * *